(12) United States Patent
Cohen

(10) Patent No.: US 6,217,565 B1
(45) Date of Patent: Apr. 17, 2001

(54) REINFORCED VARIABLE STIFFNESS TUBING

(76) Inventor: Mark Cohen, 32 Lawrence La., Palisades, NY (US) 10964

( * ) Notice: Subject to any disclaimer, the term of this patent is extended or adjusted under 35 U.S.C. 154(b) by 0 days.

(21) Appl. No.: 09/356,279

(22) Filed: Jul. 16, 1999

Related U.S. Application Data

(60) Provisional application No. 60/093,035, filed on Jul. 16, 1998.

(51) Int. Cl.$^7$ .................................................. A61M 25/00
(52) U.S. Cl. ......................... 604/525; 604/525; 604/527
(58) Field of Search ..................... 604/523–529

(56) References Cited

U.S. PATENT DOCUMENTS

| | | | |
|---|---|---|---|
| 4,425,919 | 1/1984 | Alston, Jr. et al. ................ | 128/658 |
| 4,764,324 | 8/1988 | Burnham .......................... | 264/103 |
| 5,078,702 | 1/1992 | Pomeranz ......................... | 604/280 |
| 5,085,649 | 2/1992 | Flynn .............................. | 604/282 |
| 5,221,270 | 6/1993 | Parker ............................. | 604/282 |
| 5,254,107 | 10/1993 | Soltesz ............................ | 604/282 |
| 5,312,356 | 5/1994 | Engelson et al. ................. | 604/164 |
| 5,395,332 | * 3/1995 | Ressemann et al. . | |
| 5,441,489 | 8/1995 | Utsumi et al. ................... | 604/280 |
| 5,466,222 | 11/1995 | Ressemann ....................... | 604/96 |
| 5,531,721 | 7/1996 | Pepin et al. ...................... | 604/282 |
| 5,533,987 | 7/1996 | Pray et al. ....................... | 604/280 |
| 5,538,513 | * 7/1996 | Okajima . | |
| 5,569,196 | 10/1996 | Muni ............................... | 604/96 |
| 5,603,705 | 2/1997 | Berg ................................ | 604/282 |
| 5,630,806 | * 5/1997 | Inagaki et al. . | |

* cited by examiner

Primary Examiner—Mark Bockelman
(74) Attorney, Agent, or Firm—Sheldon H. Parker

(57) ABSTRACT

A reinforced catheter having a multi-layered structure suitable for medical uses comprising an inner liner, a braided reinforced layer adjacent to the inner liner, a first resin adjacent to the braided layer, and a harder second resin overlaying the first resin; wherein, the first resin and second resin taper inversely to one another along the length of the catheter, thereby forming a co-tapered soft tip that reduces body trauma.

18 Claims, 2 Drawing Sheets

REINFORCED VARIABLE STIFFNESS TUBING

CROSS-REFERENCE TO RELATED APPLICATION

This application claims the benefit of copending provisional patent application, Ser. No. 60/093,035, filed Jul. 16, 1998, the disclosure of which is incorporated hereby, by reference, as though recited in full.

BACKGROUND OF THE INVENTION

1. Field of the Invention

The invention discloses reinforced co-tapered, variable stiffness tubing, and more specifically a reinforced tubing using an encapsulated braid.

2. Brief Description of the Prior Art

Catheterization procedures are used to diagnose the condition of a patient's body tissue such as arterial passageways or the like. Normally, an incision is made in the patient's body in order to insert the catheter apparatus into the passageways to be diagnosed. The catheter is then inserted through the incision and into the desired passageway. The catheter is fed through the passageway until it is correctly positioned adjacent the desired body organ, such as the heart. The catheter is then precisely rotated and manipulated into the desired body organ, for instance, the right coronary artery. Diagnostic fluid is then injected into the passageway at a predetermined minimum flow rate in order for a separate device, such as an x-ray; to properly record in photograph form the condition of the passageway.

Dilatation catheters predominately fall into two categories, over-the-wire catheters that are fed over a guide wire and fixed wire catheters, which serve as their own guide wire. Wireless dilatation balloon catheters have been developed in an attempt to obtain some of the advantage of an over-the-wire catheter. Dilatation catheters must offer flexibility to allow the catheter to maneuver through tight curvatures in the vascular system. The physician must also have the ability to transmit longitudinal force, from the proximal to the distal ends, to push the catheter through the guide catheter and arteries and across the stenosis.

Angioplasty is an effective method of opening stenosis in the vascular system. In the most commonly used form of angioplasty, a balloon catheter is guided through the vascular system in position across the stenosis. Once in position, the balloon is inflated, the artery opened and acceptable blood flow reestablished.

The above procedures, however, frequently induce trauma to the walls of the patient's passageways. Prior art catheters have sought to reduce this trauma by providing a highly flexible catheter that bends in conformance with the passageways. In order to allow the catheter to be fed through the passageways, the catheter must have sufficient rigidity to provide adequate torque transmission. Without sufficient torque transmission, the catheter cannot be precisely rotated into the desired body organ. Further, poor torque transmission causes buckling, wind-up and whiplash, inducing trauma to the passageways and causing pain and discomfort to the patient.

Thus, the medical profession has been faced with a trade-off between a highly flexible catheter apparatus that fails to function adequately when in torsion or a rigid catheter that creates an intolerable amount of trauma.

U.S. Pat. No. 5,805,649 issued to Flynn, discloses a Torque Controlled Tube that utilizes the co-tapering of polymeric materials, such as polyamides and polyurethanes, to produce a tube that is variable in stiffness. While this construction produces adequate pushability and kink resistance results for thick walled tubing, it does not address problems inherent in thin-walled tubing. The stiffer material is in higher concentration in the sections(s) of the tube that requires good pushability while the softer material is in higher concentration in the tube sections that require greater flexibility.

To address problems associated with thin walled tubing, many angiography and guiding catheters are constructed by encapsulating a braid for added strength and flex properties. Unfortunately, due to the construction methods of these catheters, the braid pattern remains constant throughout the entire length of the catheter, with exception of the tip region, therefore compromising performance characteristics through out the different segments of the catheter.

One method of producing a variable stiffness tube, suitable for medical device applications, is disclosed in U.S. Pat. No. 5,531,721, Multiple Member Intravascular Guide Catheter. This patent relates to the bonding/joining of multiple tube sections. These tube sections may or may not be reinforced. The difficulty in producing a catheter of this nature is that the transition from a "stiff" section to a "soft" section is not achieved continuously. Rather at each joint, a stress riser may occur that can weaken the tube's structure thereby leading to possible premature kinking when flexed or rupturing when pressurized.

Engleson, U.S. Pat. No. 5,312,356, discloses a Catheter with Low-Friction Distal Segment that utilizes a variable braided pattern to minimize jamming, stick or locking of the distal end of the catheter or any part of the guide wire against the surface. The braided material is exposed on the inner surface of the tube at the distal tip of this catheter and is not used to provide variable stiffness but rather as a means of preventing the sticking problems mentioned previously.

Many other patents have addressed the problem of minimizing body trauma during insertion of a catheter. These include the use of a glass transition material (U.S. Pat. No. 5,441,489 to Utsumi et al); a single-lumen shaft for use with either a fixed-wire balloon catheter or an innerless catheter (U.S. Pat. No. 5,533,987 to Pray et al); and a collapsible shaft and guide wire lumen (U.S. Pat. No. 5,466,222 to Ressemann et al). Muni et al (U.S. Pat. No. 5,569,196) discloses a tractable catheter having two lumens that vary in Shore hardness. In U.S. Pat. No. 5,603,705 to Berg, an intravascular catheter is constructed with an outer layer and an inner layer that is covered with a support surface, such as a stainless steel wire braid. Another dual lumen catheter that includes a wire braid between the two lumens, is disclosed in U.S. Pat. No. 5,078,702 to Pomeranz. In U.S. Pat. No. 5,254,107 to Soltesz the plastic catheter shaft has embedded the braid within the outer catheter shaft. In U.S. Pat. No. 4,764,324 to Burnham also incorporates the reinforcing member into the outer lumen by heating the lumen after molding. U.S. Pat. No. 5,221,270 to Parker discloses the use of tapered ends on the catheter materials to change from a harder Shore to a softer Shore and provide an outer diameter with a uniform, continuous outer layer.

U.S. Pat. No. 4,425,919 has sought to overcome the foregoing problems by providing a catheter with a small outside diameter and utilizing a pre-oriented substrate that adequately supports the reinforcing means. A flat braid is used which is maintained in its position around the substrate by a surrounding superstrate.

SUMMARY OF THE INVENTION

The foregoing prior art examples do not provide solutions to the current problems associated with thin walled catheters that are used for placement of medical devices.

Although the prior art illustrates attempts to provide a flexible catheter tubing with a soft tip and stiff body, in order to reduce trauma while allowing for maneuverability, they do not specifically address the current problems associated with thin walled catheters that are used for placement of medical devices. For example, the co-tapering of materials address stiffness and flexibility issues in angiography catheters where thicker walled catheters are acceptable, but do not provide sufficient strength to perform as a guide catheter. One existing problem with current guide catheter technology is that the braid pattern is constant through out the length of the catheter, therefore compromising both push and flex requirements.

Another problem that has been addressed in the prior art is that of adhering a "soft" tip to the distal end of the catheter. Many catheters use a heat or gluing process to adhere a low durometer polymeric material to the end of the catheter. Usually, these materials are in the same polymeric family, (i.e. urethanes, ethylenes, etc.) but vary in durometer and do not bond easily to the tube matrix. Pomeranz, U.S. Pat. No. 5,078,702 discloses a Soft Tip Catheter that attempts to address these bonding problems to form a stable joint. Unfortunately, this design limits the contact surface of the materials being bonded due to the presence of the inner liner.

The current invention overcomes the foregoing problems in "stiff" to "soft" transition by providing a continuous structure that is reinforced while varying in longitudinal stiffness. Further the utilization of a co-tapered soft tip reduces body trauma while selecting polymeric materials matching the contact surface maximize the bonding mechanism between the tube and the tip.

BRIEF DESCRIPTION OF THE DRAWINGS

The advantages of the instant disclosure will become apparent when read with the specification and the drawings, wherein.

DETAILED DESCRIPTION OF THE PREFERRED EMBODIMENTS OF THE INVENTION

Currently variable stiffness catheters comprise an inner most layer that is comprised of a thin fluoropolymer film. This film is then covered with a braid, which is usually metallic but also can be made of a polymer, such as nylon, high density and linear polyolefines, such as polyethylene, or a composite, such as Kevlar. The actual braid design can be single or side-by-side strands, following a traditional braid pattern. The braid is then coated with at least two component co-tapered.

The cotapered layers of tubing, extend from the proximal to distal ends. In general, the discrete layers differ in durometer as they advance distally, forming a rigid to soft composite construction. Most advantageously the structure softens in durometer from distal to proximal end.

In other applications, a soft tube having a uniform durometer is joined with the braided substrate. A non-braided soft tip is then usually bonded to the distal end. Hubs and strain relief are fitted proximally and the tip is preformed into a specific shape depending on the intended application.

In U.S. Pat. No. 5,085,649 issued on Feb. 4, 1992 to Vincent Flynn, a catheter tubing suitable for medical use is disclosed. The tubing is multi-layer and comprises an interior tubular portion, consisting of two layers, and a concentric outer shell. The two interior layers are tapered inversely for a portion of the length of the tube with at least one end of the interior portion extending beyond the concentric outer shell. Although the '649 patent provides an increased torque resistance and pushability suitable for thick walled tubing, the problems inherent with thin wall tubing are not overcome.

To enable the tubing of the disclosed invention to overcome the problems inherent with thin wall tubing, a braid is added to the variable stiffness tube to increase the resistance to kinking while maintaining the desired flexibility. The braid further increases the burst pressures and pushability of the catheter. Possibly the most valuable improvement is the increased torque control of the distal tip.

The current invention utilizes varying braid patterns encapsulated throughout the catheter to program into the tube either good pushability characteristics or good flexibility characteristics. Typically a "loose" braid pattern promotes column strength in the structure and hence enhances the pushability of the catheter while a "tight" braid pattern promotes radial reinforcement in the structure and enhances the flexibility of the tube. By providing variable patterns within a single length of tubing, a single catheter can be provided with optimum controllability.

Figure 1:
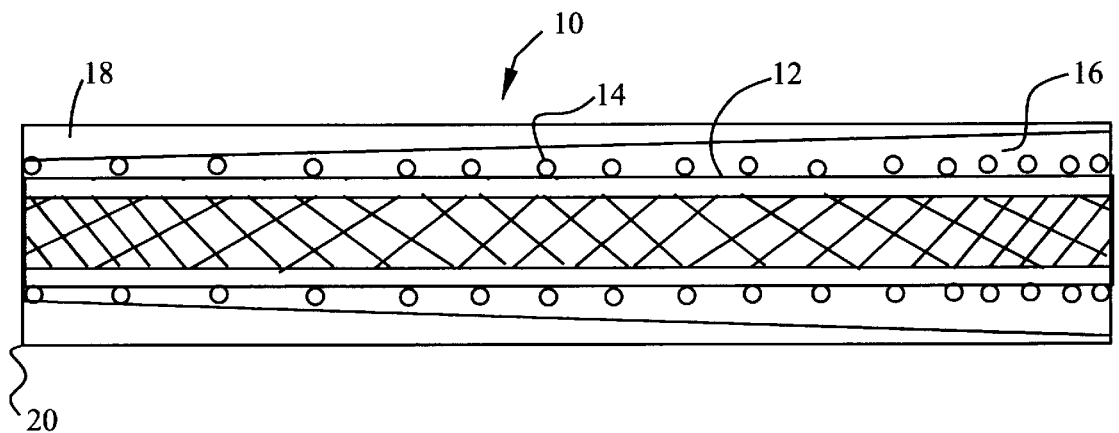
FIG. 1 is a longitudinal, cross-sectional view of the disclosed catheter.
Figure 2:
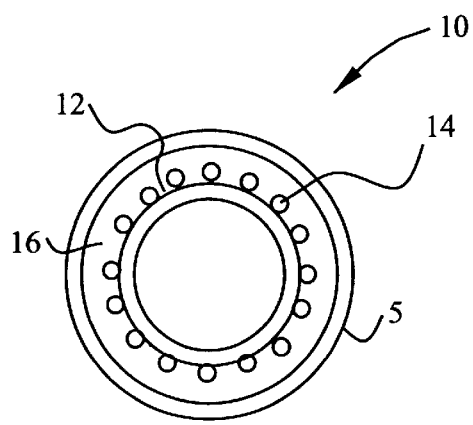
FIG. 2 is a cross-section view of the distal end of the tube of FIG. 1.

The advantage of the braid has been recognized in the prior art, such as U.S. Pat. No. 5,312,356 to Engelson et al, where the braid is used to minimize jamming, sticking or locking of the distal end of the catheter. The catheter disclosed herein utilizes the advantages provided by the braid and incorporates these with the variable stiffness tube in an easy to manufacture monolithic construction that avoids bursting and reduces body stress and trauma. The extruded construction, which incorporates the braid in a single extrusion operation, greatly reduces manufacturing expenses by providing a single step, fully automated process The catheter tube 10, as illustrated in FIGS. 1 and 2 is constructed by forming an interior liner 12 as the inner most layer. The liner 12 is then covered with a variable pitch braid 14 and then encapsulated within an interior co-taper 16 and exterior co-taper 18 that form the tube wall 20. The liner 12 is manufactured from a resin having suitable properties to provide minimal friction between a guide wire/device or fluid and the interior surface of the liner 12. Examples of these materials are a fluoropolymer or high durometer polymers (greater than 63 D Shore hardness) such as polyurethane, polyamide, polyimide, peek, polyesters, Pebax, Plexar, polyethylenes, etc. The wall thickness of the liner 12 can vary from 0.0005 inch to 0.0030 inch depending on the desired performance. The thickness of the liner 12 directly alters the flexibility and subsequently the kink resistance. By varying the thickness of the liner 12 within the catheter length, additional control over flexibility can be achieved.

The variable pitch braid 14 can be fabricated from round or profile wire stock. The braid pattern can also be formed using one; two or three wires wound parallel to and touching each other in a diamond or herringbone pattern. Typical materials used in the braid 14 are stainless steel, nickel titanium or any precious metal that could enhance the fluoroscopic visualization of the tube. Typical round wire diameters are 0.0005 inch to 0.005 inch with profile wire sizes varying from a width to height ratio of 1:1 to 8:1 with the minimum height of 0.0005 inch to a maximum width of 0.005 inch. The braid pattern, defined in pics per inch (ppi) will vary depending upon the desired pushability. In regions where pushability is required the pattern will be in the range from about 10 to 40 ppi while in regions where flexibility and kink resistance is essential, the pattern will be in the range of from about 50 to 150 ppi. In addition to changing the ppi, adjusting the diameter of the wire, as well as width to height ratio will further alter the pushability characteristics of the catheter.

The interior layer 16 tapers longitudinally along a portion of the tube 10, with the concentration of material increasing from the proximal end to the distal end. The interior co-taper 16 is generally manufactured from a material having a low durometer (80 A–40 D) and preferably is polymer compatible for thermal bonding to the liner 12. In specialized applications, however, the durometer may be increased and will be evident to those skilled in the art. Typical materials used for the interior co-taper 16 are low durometer polyurethane, polyamide, polyimide, peek, polyesters, pebax, polyethylenes, etc. The percent concentration for the interior co-taper 16 can be as little as 1% of the total tube wall 20 at the proximal end and increase to as much as 99.9% of the total tube wall 20 at the distal end. This concentration can taper linearly through out the length of the catheter or transition from over a length of about 2 inches to about 9 inches. The taper is dependent upon the length of the catheter and end use, and will become apparent to those skilled in the art.

The exterior jacket layer 18 tapers longitudinally with decreasing concentrations of material from the proximal to distal ends. The exterior co-taper 18 must be capable of thermal bonding to the interior co-taper 16 and have a high durometer (60 D–85 D). Again, typically materials used for this layer are high durometer, polyurethane, polyamide, polyimide, peek, polyesters, pebax, polyethylenes, etc. As with the interior co-taper 16, the percent concentration can be as little as 1% or as much as 99.9% of the total tube wall 20.

Figure 3:
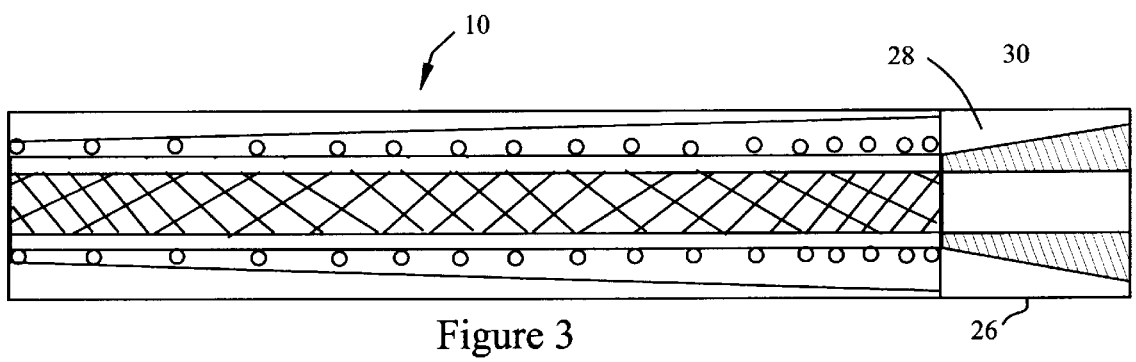
FIG. 3 is a longitudinal, cross-sectional view of the catheter of FIG. 1 with a two layered, co-tapered tip attached to the distal end.

FIG. 3 depicts the disclosed tube 10 with a two layer, co-tapered tip 26 attached to the distal end. The inner tip layer 30 tapers longitudinally with an increasing concentration of material from the proximal end to the distal end. The inner tip layer is usually manufactured from a low durometer (80 A–40 D) material to minimize trauma to the vessel walls. The polymeric material must be capable of being thermal bonded to the liner 12 as well as to the exterior tip layer 28. Typical materials used for this layer are low durometer polyurethane, polyamide, polyimide, peek, polyesters, pebax, polyethylenes, etc. The concentrations of this material are as little as 1% of the total tip 26 proximally and increase to as much as 99% of the total tip 26 distally. The exterior tip layer 28 typically tapers longitudinally with decreasing concentrations of material, from the proximal to distal ends of the tip 26. The high durometer (60 D–85 D) polymeric material use to manufacture the exterior tip layer 28 must be capable of thermal bonding to the liner 12, the interior co-taper 16, the exterior co-tapered 18 and the exterior tip layer 28. This material can be selected from the group of materials listed heretofore. Usually the materials selected for manufacturing the interior co-taper 16 and the exterior tip layer 28 are identical in polymeric structure and hardness. As an alternate embodiment, grinding the distal end of the tube exterior layer 28, as disclosed in U.S. Pat. No. 5,085,649 as issued to Flynn to expose the softer, interior co-tapered layer 30 is used to create the tip rather than affixing a separate constructed tip.

Figure 4:
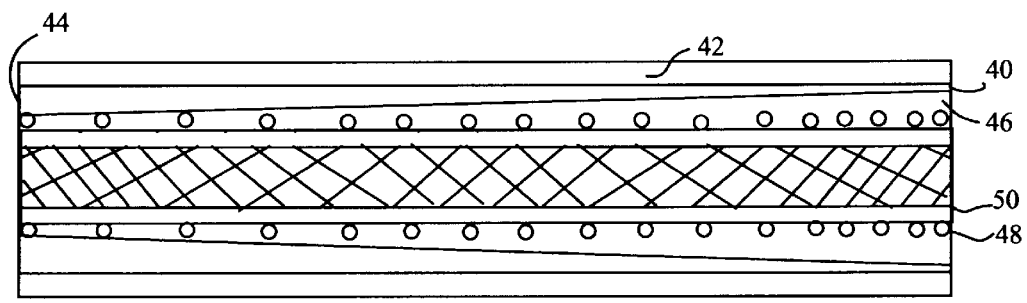
FIG. 4 is a longitudinal cross-sectional view of a three layer co-taper system over a braid.

In an alternate embodiment, the tubing 40 can consist of three outer layers over the braid, as illustrated in FIG. 4. In this embodiment the central core 50 is covered with the braid 48, interior layer 46 and mid-layer 44. These correspond to the layers set forth in response to FIG. 1. The additional exterior layer 42 and has been added to further customize the properties of the catheter; the durometer varying based on the end use.

A variation to the polymeric structure is the inclusion of a radiopaque compound into the tip material to enhance fluoroscopic visualization. These radiopaque compounds are usually available in either powder or concentrate form and are made of heavy metal materials such as tungsten, barium sulfate, bismuth trioxide, tantalum, etc.

Additional detail for manufacture of the co-tapered tubing can be found in U.S. Pat. No. 5,085,649 issued Feb. 4, 1992 to Vincent J. Flynn, which is incorporated herein as though recited in full.

The interior diameter of the liner 12 affects the overall interior diameter of the end use catheter and all dimensions must be adjusted accordingly. The addition of the additional layers, either on the interior or exterior, can also be used to produce variable stiffness tube.

Each layer within the disclosed tube possesses different physical properties, tailored to satisfy multiple purposes. By discretely feeding the braided substrate portion into the co-tapered construction the bonding of soft tips can be eliminated. This construction eliminates the multiple joints that are present in many prior art construction methods. The continuous transition from hard to soft provides a natural transition, in contrast to prior art constructions that have abrupt changes at welds, increasing kinking tendencies when bent.

What is claimed is:

1. A reinforced catheter having a multi-layer structure suitable for medical uses comprising:
    an inner liner,
    a braided reinforcing layer, said braided reinforcing layer being adjacent said first inner liner and having at least one braiding pattern,
    a first resin, said first resin being a concentric layer adjacent said braided reinforcing layer, and
    a second resin, said second resin being a concentric layer overlaying said first resin,
    said catheter having a first point along its-length and a second point spaced distally from said first point, the thickness of said first resin having an increasing taper from said first point to said second point and the thickness of said second resin tapering inversely to the taper of said first resin from said first point to said second point to form a co-tapered soft tip, the hardness of said second resin exceeding the hardness of said first resin, whereby said co-tapered soft tip reduces body trauma.

2. The reinforce catheter of claim 1 wherein said second resin is ground to expose said first resin thereby increasing flexibility of said co-tapered tip.

3. The reinforced catheter of claim 1 wherein each of said at least one braiding pattern is a plurality of braiding patterns having at least two different braiding patterns, thereby varying the torque control, kink resistance and pushability of said catheter within said catheter length.

4. The reinforced catheter of claim 3 wherein said braid varies in pic rate thereby providing varying radial reinforcement and flexibility.

5. The reinforced catheter of claim 4 wherein said braid is made from a material selected from the group consisting of stainless steel, nickel, and titanium.

6. The reinforced catheter of claim 3 wherein said braid is made from a composite polymeric material.

7. The reinforced catheter of claim 3 wherein said braid is made from a material selected from the group consisting of high density and linear polyolefins, polyesters, and carbon fiber.

8. The reinforced catheter of claim 3 wherein said braid pattern has a region of optimized pushability with a braid pattern in the range from about 10 to 40 ppi and a region of optimized flexibility and kink resistance with a braid pattern in the range of from about 50 to 150 ppi.

9. The reinforced catheter of claim 1 wherein said braid is a precious metal thereby enhancing the fluoroscopic visibility of said catheter.

10. The reinforced catheter of claim 1 wherein said braid is a round wire having a diameter in the range from about 0.0005 to 0.005 inch.

11. The reinforced catheter of claim 10 wherein said braid pattern has a region of optimized pushability with a braid pattern in the range from about 10 to 40 ppi and a region of optimized flexibility and kink resistance with a braid pattern in the range of from about 50 to 150 ppi.

12. The reinforced catheter of claim 1 wherein said braid is a wire having a wire profile varying from a width to height ratio of 1:1 to 8:1, and having a minimum height of 0.0005 and a maximum width of 0.005 inch.

13. The reinforced catheter of claim 12 wherein said braid pattern has a region of optimized pushability with a braid pattern in the range from about 10 to 40 ppi and a region of optimized flexibility and kink resistance with a braid pattern in the range of from about 50 to 150 ppi.

14. The reinforced catheter of claim 1 wherein said first resin and said second resin are at least two materials of different durometers.

15. The reinforced catheter of claim 1 wherein said inner liner has a low friction interior surface, said interior surface comprising a material selected from the group consisting of a fluropolymer, polyamid and polyethylene.

16. The reinforced catheter of claim 1 wherein said second resin has a durometer of at least 55 D.

17. The reinforced catheter of claim 1 wherein said resin surfaces are modified by chemical etching.

18. The reinforced catether of claim 1 further comprising a concentric outer layer, said concentric outer layer being adjacent to said second resin thereby customizing properties of said catheter.

* * * * *